United States Patent [19]

Ebmeyer et al.

[11] Patent Number: 5,672,748
[45] Date of Patent: Sep. 30, 1997

[54] PROCESS FOR PREPARING TRIFLUOROACETYL FLUORIDE

[75] Inventors: Frank Ebmeyer, Augsburg; Tobias Metzenthin, Frankfurt; Günter Siegemund, Hofheim, all of Germany

[73] Assignee: Solvay, Brussels, Belgium

[21] Appl. No.: 496,634

[22] Filed: Jun. 29, 1995

[30] Foreign Application Priority Data

Jul. 4, 1994 [DE] Germany .................. 44 23 386.8

[51] Int. Cl.$^6$ .................................. C07C 51/58
[52] U.S. Cl. .................................... 562/852
[58] Field of Search .............................. 562/852

[56] References Cited

U.S. PATENT DOCUMENTS 3,787,489 1/1974 Antonini et al. .
3,859,424 1/1975 Scherer et al. .
4,547,483 10/1985 Müller et al. .................. 502/226

FOREIGN PATENT DOCUMENTS 0 130 532 1/1985 European Pat. Off. .
976316 7/1963 United Kingdom .

*Primary Examiner*—Paul J. Killos
*Attorney, Agent, or Firm*—Connolly & Hutz

[57] ABSTRACT

The invention relates to the preparation of trifluoroacetyl fluoride by reacting trichloroacetyl chloride with anhydrous hydrogen fluoride in the gaseous phase on a catalyst which is obtainable by reacting a water-soluble chromium (III) salt with magnesium hydroxide or magnesium oxide in the presence of water, converting the reaction mixture into a paste, drying the paste and treating it with hydrogen fluoride.

20 Claims, No Drawings

PROCESS FOR PREPARING TRIFLUOROACETYL FLUORIDE

The invention relates to a process for preparing trifluoroacetyl fluoride by reacting trichloroacetyl chloride with anhydrous hydrogen fluoride in the gas phase in the presence of a chromium-containing fluorination catalyst.

Trifluoroacetyl fluoride is used as a starting compound for the preparation of numerous active compounds in the pharmaceutical and crop protection sector or for the preparation of trifluoroacetic acid.

The fluorination of trichloroacetyl chloride by reaction with hydrogen fluoride in the presence of a fluorination catalyst comprising chromium (III) oxide in the gas phase at 250°–325° C. is already known. However, in this reaction, chlorodifluoroacetyl fluoride is chiefly formed (GB-B 976 316), while in a complete fluorination to give trifluoroacetyl fluoride, 26% of the trichloroacetyl chloride is lost due to decomposition (U.S. Pat. No. 3,859,424).

According to U.S. Pat. No. 3,787,489, the fluorination of trichloroacetyl chloride to give trifluoroacetyl fluoride is performed using a chromium catalyst in a reactor which contains three hot zones at different temperatures in order to avoid undesirable decomposition reactions. The catalyst must be packed in the three heating zones in different layers heated to different temperatures, which layers themselves are separated by intermediate layers of alumina. This complicated catalyst packing is difficult to realize industrially and furthermore impedes exchange and cleaning of the catalyst bed.

It has now surprisingly been found that, when a known chromium- and magnesium-containing fluorination catalyst is used, reactor operation with three zones heated to different temperatures is not necessary.

The invention relates to a process for preparing trifluoroacetyl fluoride by reacting trichloroacetyl chloride with anhydrous hydrogen fluoride in the gas phase, which comprises using a chromium- and magnesium-containing catalyst which is obtainable by precipitating out chromium (III) hydroxide by reacting 1 mol of a water-soluble chromium (III) salt with at least 1.5 mol of magnesium hydroxide or magnesium oxide in the presence of water, converting the reaction mixture into a paste which contains chromium hydroxide and a magnesium salt and then drying the paste and treating it with hydrogen fluoride at temperatures of 20° to 500° C.

The catalyst and its pretreatment (activation) is described in EP-B-0 130 532 (=U.S. Pat. No. 4,547,483), the teaching of which is hereby expressly incorporated by reference. For every mol of Cr (III) salt at least 1.5 mol of Mg(OH)$_2$ or MgO are used.

The process is generally carried out in the manner of conventional gas reactions on fixed-bed catalysts by passing the gas mixture of trichloroacetyl chloride and hydrogen fluoride through a heatable reaction tube which is packed with the catalyst according to the claims.

The reaction tube is preferably mounted vertically and comprises a material sufficiently resistant to hydrogen fluoride, such as nickel or steel.

To carry out the process, trichloroacetyl chloride and hydrogen fluoride are mixed in the gaseous state. Transport of the starting materials for this purpose can be performed either in the gaseous state (by heating the reservoirs and feed lines) or in the liquid state (by using feed pumps). The starting materials are then passed through a preheater or an evaporator into the catalyst-packed reactor. The starting substances are advantageously added continuously and used in technical-grade purity.

At atmospheric pressure, the throughput of trichloroacetyl chloride is expediently 5–800 grams (approximately 0.03 to 4.4 mol), in particular 30–300 grams (approximately 0.2 to 2 mol), per liter of catalyst and hour. At higher pressures, the throughput can be correspondingly higher.

The process generally takes place at atmospheric pressure or a slight superatmospheric pressure, about $10^{-1}$ to 25 bar, preferably 1 to 12 bar. In particular, to achieve higher space-time yields, the use of superatmospheric pressure (2 to 12 bar) is to be preferred.

The molar ratio of hydrogen fluoride to trichloroacetyl chloride is generally 4:1 to 15:1, preferably 5:1 to 12:1.

The reaction is generally carried out at temperatures of 200° to 400° C., preferably at 250° to 370° C., in particular at 270° to 340° C.

The residence time of the gas mixture in the reactor is generally 1 to 60 s, preferably 5 to 50 s.

The conversion of the trichloroacetyl chloride used is generally complete.

The gas formed in the reaction and containing trifluoroacetyl fluoride, HCl and HF is condensed and worked up by distillation.

The advantages of the process according to the invention are the simple procedure with only one reaction zone, the high conversion rate of trichloroacetyl chloride and the high selectivity of the formation of trifluoroacetyl fluoride. A further important advantage is that, despite the simple procedure with only one reaction zone, no decomposition reactions occur.

The process according to the invention is explained in more detail by the examples below. The conversion rate attained is 100% in all the examples. The percentages in the examples are by weight, unless otherwise stated.

Experimental report (Catalyst preparation according to EP-B-130 532=U.S. Pat. No. 4,547,483)

200 g of Cr(NO$_3$)$_3$ . 9 H$_2$O were dissolved in 1 l of water. This solution was added to a mixture of 500 g of magnesium oxide and 240 g of graphite and the pasty mass forming in this process was intimately kneaded.

The pasty reaction product was then granulated to form cube shapes (0.5 cm edge length) and dried at 100° C. for 16 hours.

1 l (bulk volume) of the dried catalyst bodies (=approximately 1000 g) was treated with 15 mol of hydrogen fluoride at 200° C. in a tube made of nickel or VA stainless steel having an open width of 5 cm and a length of 100 cm. The duration of the hydrogen fluoride treatment was approximately 6 hours. In the treatment, the HF was diluted with N$_2$. The fluorination catalyst obtained (chrome magnesite catalyst) had a chromium content of 2.3% by weight.

EXAMPLE 1

The reactor used for the reaction was a nickel tube having an internal diameter of 5 cm and a length of 120 cm, which tube was evenly heated externally using an oil heater. The internal temperature of the reactor was determined using an axial thermocouple in a housing. The vertically installed reactor was charged with 1.0 kg (1.0 l) of the chrome magnesite catalyst prepared according to the experimental report.

The reaction partners anhydrous hydrogen fluoride (purity >99%) and trichloroacetyl chloride (purity >99%) were fed into an upstream evaporator heated to 125° C. Here there proceeded mixing and vaporization of the reaction partners, which were then run in the gaseous state into the reactor evenly heated to an internal temperature of 340° C. and packed with the catalyst. At a feed rate of 65.1 g/h of hydrogen fluoride and 61.9 g/h of trichloroacetyl chloride, analysis of the gas mixture exiting from the reactor gave the following result:

Trifluoroacetyl fluoride: 83%

Difluoromonochloroacetyl fluoride: 17%

Fluorodichloroacetyl fluoride: 0%

Trichloroacetyl fluoride: 0%

Decomposition products, such as fluorinated Cl compounds had not formed.

EXAMPLE 2

The procedure was followed as in Example 1, except that 57 g/h of trichloroacetyl chloride and 76 g/h of hydrogen fluoride were fed in. Analysis of the gas mixture exiting from the reactor gave the following result:

Trifluoroacetyl fluoride: 86%

Difluoromonochloroacetyl fluoride: 14%

Fluorodichloroacetyl fluoride: 0%

Trichloroacetyl fluoride: 0%

Decomposition products had not formed.

EXAMPLE 3

The reactor used was an electrically heated tube made of V4A stainless steel having an internal diameter of 5 cm and a length of 70 cm, which tube was packed with 1.1 kg of the chrome magnesite catalyst prepared according to the experimental report. The thermal gradient was determined using an axial thermocouple and was in the present case 270° C. at the coldest point and 340° C. at the hottest point of the catalyst packing. The reaction partners anhydrous hydrogen fluoride and trichloroacetyl chloride were passed into an evaporator section, heated to 160° C., in the form of a 30 cm long V4A tube. The mixed components then passed into the electrically heated reactor where the reaction to give trifluoroacetyl fluoride took place. At a feed rate of 28 g/h of trichloroacetyl chloride and 28 g/h of hydrogen fluoride, analysis of the gas exiting from the reactor gave the following result:

Trifluoroacetyl fluoride: 94.3%

Difluoromonochloroacetyl fluoride: 5.7%

Decomposition products such as fluorinated Cl compounds or derivatives of the phosgene or difluorophosgene resulting from a decomposition of trichloroacetyl chloride had not formed.

EXAMPLE 4

45 g/h of trichloroacetyl chloride and 46 g/h of anhydrous hydrogen fluoride were metered into the reactor described in Example 3. The two reaction partners were passed through the 250°–260° C. evaporator section into the reactor whose temperature was 270° C. at the coldest point and 340° C. at the hottest point (catalyst packing 1.1 kg of chrome magnesite catalyst according to the experimental report). Regular analysis of the gases exiting from the reaction zone in the course of an operating time of 5 h gave the following composition:

Trifluoroacetyl fluoride: 86.0%

Difluoromonochloroacetyl fluoride: 14.0%

Other products had not formed.

EXAMPLE 5

40 g/h of hydrogen fluoride and 38 g/h of trichloroacetyl chloride were metered into the reactor described in Example 3 via the evaporator section preheated to 271° C. At a temperature distribution between a minimum of 260° C. and a maximum of 390° C., the reaction gave a product gas having the following composition:

Trifluoroacetyl fluoride: 95.4%

Difluoromonochloroacetyl fluoride: 3.4%

Fluorodichloroacetyl fluoride: 0.6%

Difluorophosgene: 0.6%

Trichloroacetyl fluoride: 0.0%

Other byproducts had not formed.

We claim:

1. A process for preparing trifluoroacetyl fluoride by reacting trichloroacetyl chloride with anhydrous hydrogen fluoride in the gas phase, which comprises using a chromium- and magnesium-containing catalyst which is obtainable by precipitating out chromium (III) hydroxide by reacting 1 mol of a water-soluble chromium (III) salt with at least 1.5 mol of magnesium hydroxide or magnesium oxide in the presence of water, converting the reaction mixture into a paste which contains chromium hydroxide and a magnesium salt and then drying the paste and treating it with hydrogen fluoride at temperatures of 20° to 500° C.

2. The process as claimed in claim 1, wherein the reaction of trichloroacetyl chloride with hydrogen fluoride is carried out in the temperature range 200°–400° C.

3. The process as claimed in claim 1, wherein the reaction of trichloroacetyl chloride with hydrogen fluoride is carried out in the temperature range 250°–370° C.

4. The process as claimed in claim 1, wherein the reaction of trichloroacetyl chloride with hydrogen fluoride is carried out at a pressure of 1–12 bar.

5. The process as claimed in claim 1, wherein the reaction of trichloroacetyl chloride with hydrogen fluoride is carried out at a molar ratio of 4 to 15 mol of HF per mole of trichloroacetyl chloride.

6. A process for preparing trifluoroacetyl fluoride by reacting trichloroacetyl chloride with anhydrous hydrogen fluoride in the gas phase, which comprises using a chromium- and magnesium-containing catalyst which contains at least 55% by weight of magnesium fluoride and 0.5 to 29% by weight of chromium, the atomic ratio of magnesium to chromium being between 1.5 to 50.

7. The process as claimed in claim 6, wherein the catalyst is obtainable by precipitating out chromium (III) hydroxide by reacting 1 mol of a water-soluble chromium (III) salt with at least 1.5 mol of magnesium hydroxide or magnesium oxide in the presence of water, converting the reaction mixture into a paste which contains chromium hydroxide and a magnesium salt and then drying the paste and treating it with hydrogen fluoride at temperatures of 20° to 500° C.

8. The process as claimed in claim 7, wherein the reaction of trichloroacetyl chloride with hydrogen fluoride is carried out in the temperature range 200°–400° C.

9. The process as claimed in claim 7, wherein the reaction of trichloroacetyl chloride with hydrogen fluoride is carried out in the temperature range 250°–370° C.

10. The process as claimed in claim 7, wherein the reaction of trichloroacetyl chloride with hydrogen fluoride is carried out at a pressure of 1–12 bar.

11. The process as claimed in claim 7, wherein the reaction of trichloroacetyl chloride with hydrogen fluoride is carried out at a molar ratio of 4 to 15 mol of HF per mole of trichloroacetyl chloride.

12. The process as claimed in claim 1, wherein the reaction of trichloracetyl chloride with hydrogen fluoride is carried out in the temperature range 270° to 340° C. and the reaction of trichloroacetyl chloride with hydrogen fluoride is carried out at a molar ratio of 5 to 12 mol of HF per mole of trichloroacetyl chloride.

13. The process as claimed in claim 7, wherein the reaction of trichloracetyl chloride with hydrogen fluoride is carried out in the temperature range 270° to 340° C. and the reaction of trichloroacetyl chloride with hydrogen fluoride is carried out at a molar ratio of 5 to 12 mol of HF per mole of trichloroacetyl chloride.

14. The process according to claim 12, wherein the reaction of trichloroacetyl chloride with hydrogen fluoride is carried out at a pressure of 1–12 bar.

15. The process according to claim 13, wherein the reaction of trichloroacetyl chloride with hydrogen fluoride is carried out at a pressure of 1–12 bar.

16. The process according to claim 14, wherein the process produces a gas mixture exiting from the reactor which comprises a) 83 to 95% trifluoroacetyl fluoride, b) 3.4 to 17% difluoromonochloroacetyl fluoride, and c) 0 to 0.6% fluorodichloroacetyl fluoride and with the proviso that no trichloroacetyl fluoride is present.

17. The process according to claim 15, wherein the process produces a gas mixture exiting from the reactor which comprises a) 83 to 95% trifluoroacetyl fluoride, b) 3.4 to 17% difluoromonochloroacetyl fluoride, and c) 0 to 0.6% fluorodichloroacetyl fluoride and with the proviso that no trichloroacetyl fluoride is present.

18. The process according to claim 16, wherein the gas mixture exiting from the reactor consists essentially of trifluoroacetyl fluoride and difluoromonochloroacetyl fluoride.

19. The process according to claim 17, wherein the gas mixture exiting from the reactor consists essentially of trifluoroacetyl fluoride and difluoromonochloroacetyl fluoride.

20. The process according to claim 1, wherein the reaction operates at one temperature and not at different temperatures.

* * * * *